United States Patent [19]
Hilgers et al.

[11] Patent Number: 5,976,538
[45] Date of Patent: Nov. 2, 1999

[54] ADJUVANT COMPOSITION CONTAINING SYNTHETIC HYDROPHOBIC LIPOPOLYSACCHARIDE

[75] Inventors: Lucas A.T. Hilgers; Peter-Paul L.I. Platenburg, both of Weesp, Netherlands

[73] Assignee: American Cyanamid Company, Madison, N.J.

[21] Appl. No.: 08/748,787

[22] Filed: Nov. 15, 1996

Related U.S. Application Data

[63] Continuation of application No. 08/487,541, Jun. 7, 1995, abandoned, which is a continuation of application No. 08/271,586, Jul. 7, 1994, abandoned, which is a continuation of application No. 07/992,645, Dec. 18, 1992, abandoned.

[30] Foreign Application Priority Data

Dec. 23, 1991 [EP] European Pat. Off. ............... 91203383

[51] Int. Cl.$^6$ ........................ A61K 39/106; A61K 9/127; A61K 39/335; A61K 31/715
[52] U.S. Cl. ..................................... 424/184.1; 424/278.1; 424/283.1; 424/812; 424/827; 424/197.11; 424/196.11; 424/193.1; 424/194.1; 514/937; 514/54
[58] Field of Search .............................. 424/184.1, 278.1, 424/283.1, 812, 827, 197.11, 196.11, 193.1, 194.1; 514/937, 54

[56] References Cited

U.S. PATENT DOCUMENTS

| | | | |
|---|---|---|---|
| 3,919,411 | 11/1975 | Glass et al. | 424/81 |
| 4,395,354 | 7/1983 | Gutnick et al. | |
| 4,606,918 | 8/1986 | Allison et al. | |
| 4,770,874 | 9/1988 | Allison et al. | |
| 4,772,466 | 9/1988 | Allison et al. | |
| 4,933,179 | 6/1990 | Allison et al. | |
| 5,026,557 | 6/1991 | Estis et al. | |
| 5,143,848 | 9/1992 | Scholten et al. | |
| 5,376,369 | 12/1994 | Allison et al. | |
| 5,422,109 | 6/1995 | Brancq et al. | |
| 5,531,925 | 7/1996 | Landh et al. | |
| 5,552,141 | 9/1996 | Ribi . | |
| 5,554,372 | 9/1996 | Hunter . | |
| 5,559,078 | 9/1996 | Garst . | |
| 5,622,649 | 4/1997 | Hunter et al. | |
| 5,741,502 | 4/1998 | Roberts . | |
| 5,804,199 | 9/1998 | Aasjord et al. | |

FOREIGN PATENT DOCUMENTS

| | | |
|---|---|---|
| 17669 | 12/1988 | Australia . |
| 0295749 | 12/1988 | European Pat. Off. . |
| 0549074 B1 | 1/1999 | European Pat. Off. . |
| 9200101 | 1/1992 | WIPO . |

OTHER PUBLICATIONS

Int. Archs Allergy Appl. Immun. 80:320–325 (1986) "Suppression of the Cellular Adjuvanticity of Lipophilic Amines by a Polyanion".
Vaccine, vol. 11, Issue 3, 1993 "Adjuvants—a balance between toxicity and adjuvanticity".
Veterinary Bulletin, vol. 57: 881–896, Nov., 1987 "The Application of Adjuvants to Veterinary Medicine".
Medical Virology, vol. 2: 169–174 (1992) "Adjuvants for Viral Vaccines".
Klin Wochenschr (1984) 62:254–264 "Immunostimulation Clinical and Experimental Perspectives".
J. Vet Pharmacol. Therap. 9, 119–139, 1986 "A review of immunomodulators and their application in veterinary medicine".
Immunology Today, vol. 14, No. 6, 1993 "Immunostimulants".
JNCI, vol. 70, No. 5, May 1983 "Biological Response Modifiers".
Snippe et al Int. Archs Allergy Appl Immunol 65:390–398, 1981.
Elworthy et al, J. Pharm Pharmac. 21:Suppl 705–785, 1969.
Florence et al, J. Pharm Pharmac 23:153–169, 1971.
Byars et al Vaccine 5:223–228, 1987.
*The Journal of Immunology*, vol. 133, No. 6, Dec. 1984, pp. 3167–3175, Robert L. Hunter and Beth Bennett, "The Adjuvant Activity of Nonionic Block Polymer Surfactants".
Hilgers et al, Immunology, 60(1): 141–146, 1987.
Hunters et al, J. Immunology 127(3): 1244–1250, 1981.
Hilgers et al, Int. Archs Allergy Appl. Immunol. 79:392–396, 1986.

*Primary Examiner*—Nita Minnifield
*Attorney, Agent, or Firm*—Stevens, Davis, Miller & Mosher, L.L.P.

[57] ABSTRACT

According to the present invention the adjuvants comprise an emulsion containing at least one synthetic hydrophobic lipopolysaccharide, which can either or not be provided with anionic groups, while maintaining the overall hydrophobicity, an interface-forming constituent (such as an oil) and optionally an aqueous solute. In particular the adjuvant and vaccines prepared with it contain a lipopolysaccharide which had an HLB value of less then 9, more favorably less than 4.

8 Claims, 1 Drawing Sheet

ADJUVANT COMPOSITION CONTAINING SYNTHETIC HYDROPHOBIC LIPOPOLYSACCHARIDE

This application is a continuation of Ser. No. 08/487,541, filed Jun. 7, 1995, abandoned; which is a continuation of Ser. No. 08/271,586, filed Jul. 7, 1994, now abandoned, which is a continuation of Ser. No. 07/992,645, filed Dec. 18, 1992, now abandoned.

The present invention is concerned with adjuvants and with vaccines containing these adjuvants.

According to the present invention the adjuvants comprise an emulsion containing at least one synthetic hydrophobic lipopolysaccharide, which can either or not be provided with anionic groups, while maintaining the overall hydrophobicity, an interface-forming constituent and optionally an aqueous solute.

These adjuvants can be used in the preparation of veterinary or human vaccines.

The polysaccharides forming part of said synthetic hydrophobic lipopolysaccharides are esterified with straight or branched lipid groups of 8 to 40 carbon atoms; these lipid groups may be aliphatic or unsaturated, and optionally may contain an aromatic group. The mean ratio of lipid groups to sugar groups of the polysaccharides preferably is between 0.2 and 4, and more in particular can be about 1.

Optionally the lipopolysaccharide can be equipped with anionic groups, such as phosphate, sulfate, nitrate or carboxyl groups, preferably sulfate groups, while maintaining the overall hydrophobicity. Preferably, the mean ratio of anionic group to sugar groups is between 0.1 and 2.

Hydrophobicity of Synthetic LipopolySaccharide, such as Sulfo LipopolySaccharides (which are used in the examples) (hereinafter "SLPs") is defined by the hydrophilic-lipophilic-balance (HLB)-value determined according to the method of Griffin (W. C. Griffin, J. Soo. Cosmet. Chem., 1, 311, 1949) and cited by Porter (M. R. Porter, Handbook of surfactants, Blackie, Glasgow and London, 1991, page 42) which is based on the appearance of a surfactant in water. HLB-values of the hydrophobic SLPs are below 9 (i.e. insoluble, poor and unstable dispersion or stable opaque dispersion), and in particular it can be below 4 (i.e. insoluble).

Examples of interface-forming constituents are:
 a. liquids immiscible with an aqueous phase e.g. mineral, animal, vegetable or synthetic oil or other organic liquid,
 b. insoluble salts e.g. $Al(OH)_3$, $AlPO_4$, calcium-oxalate, vermiculite, bentonite, silica.
 c. microparticles/microspheres of one or multiple polymers or copolymers e.g. polyacrylate, poly(methylmethacrylate), polycyanoacrylate, polysaccharides, polypeptides, poly(ethylene-vinyl acetate), poly(lactic acid), poly(glycolic acid), poly(lactic/glycolic acid), polyoxyethylene-polyoxypropylene, polyethyleneimine, polyamidoamine.
 d. lipid bilayers of lipophilic agents e.g. phospholipids, quaternary amines.
 e. micelles of one or more of the following surface-active agents:
  anionic (e.g. carboxylates, polyalkoxycarboxylates, N-acylsarcosinates, acylated protein hydrolysates, sulfonates, alkylbenzenesulfonates, sulfonates with ester linkages, sulfonates with amide linkages, sulfonates with ether linkages, alcohol sulfates, phosphate esters),
  nonionic (e.g. ethoxylates, alcoholethoxylates, carboylic acid esters, glycerolesters, polyoxyethylene esters, carboxylic amides, polyoxyethylene fatty acid amide, polyalkylene oxide block copolymers),
  cationic (e.g. amines, oxygen containing amines, 2-alkyl-1-(2-hydroxyethyl)-2-imidazolines, quaternary amines), and
  amphoteric (e.g. imidazolinium derivatives) surface-active agents.

From the partical point of view, interface-forming substances which give in combination with the SLP stable formulations and which are well tolerated by the recipients (either animals or humans) are preferred. In this respect, oils of animal and vegetable origin, insoluble salts such as $Al(OH)_3$ and $AlPO_4$, and lipid bilayers of phospholipids of animal or vegetable origin are particularly suitable.

In the examples described below, mineral oil or squalane is used as interface-forming constituent. Squalane is preferred as this is an oil of animal origin and therefore biocompatibility and biodegrability are expected.

Examples (with various trade names) of surface-active agents with appropriate hydrophilic/lipophilic balance (HLB) value to improve the stability of oil-in-water or water-in-oil emulsions are:
 a. anionic surfactants e.g. SANDOPAN™ KST;
 b. nonionic surfactants e.g. BRIJ™ type numbers 30, 35, 58, 98, 721, TRITON™ type numbers N-57, X-100, X-102, SPAN™ type numbers 20, 40, 60, 80, 85, TWEEN™ type numbers 20, 21, 40, 60, 80, 85, PLURONIC™ type numbers PE 10100, PE 10500, RPE 2510, RPE 2520.
 c. cationic surfactants e.g. ARQUAT™ 2HT-75, AROSURF™ TA100, bis(hydrogenated tallow alkyl) dimethylammonium chloride,
 d. amphoteric surfactants e.g. LONZAINE™ type numbers 10S, 12C, 16S, SCHEROTAINE™ types CAB, IAB, MAB, AMPHOSOL™.

In the experiments described below a nonionic surfactant and especially Tween 80 was used to stabilize the emulsion of SLP and oil.

Examples of animal oils are squalane and squalene. Suitable plant oils can be obtained from soya, peanut, sesame seeds, palm, etcetera. Examples of mineral oils are MARKOL™ 52, KRAKEL™, KREMOL™, etc.

Aqueous solutes for use in the adjuvant according to the present invention are e.g. saline, phosphate buffered saline or pure water.

The adjuvant according to the invention preferably is prepared either by first mixing the synthetic hydrophobic lipopolysaccharide and the oil, and further dispersing the oily mess in water or by first mixing the lipopolysaccharide with a surface-active agent, adding water, and dispersing the oil in the water phase obtained.

The adjuvant is intended to use in vaccines for humans and animals. The vaccine can contain antigenic material characteristic for viruses, bacteria, mycoplasma or parasites, or for any other entity against which an immune response is intended to be raised. The antigenic material can for example consist of or contain live organisms, inactivated organisms, or so-called subunits (the latter e.g. prepared synthetically, or by recombinant DNA methods, or isolated from the intact organisms). For the preparation of the vaccines the antigenic material is mixed either well before or just prior to use.

Figure 1:
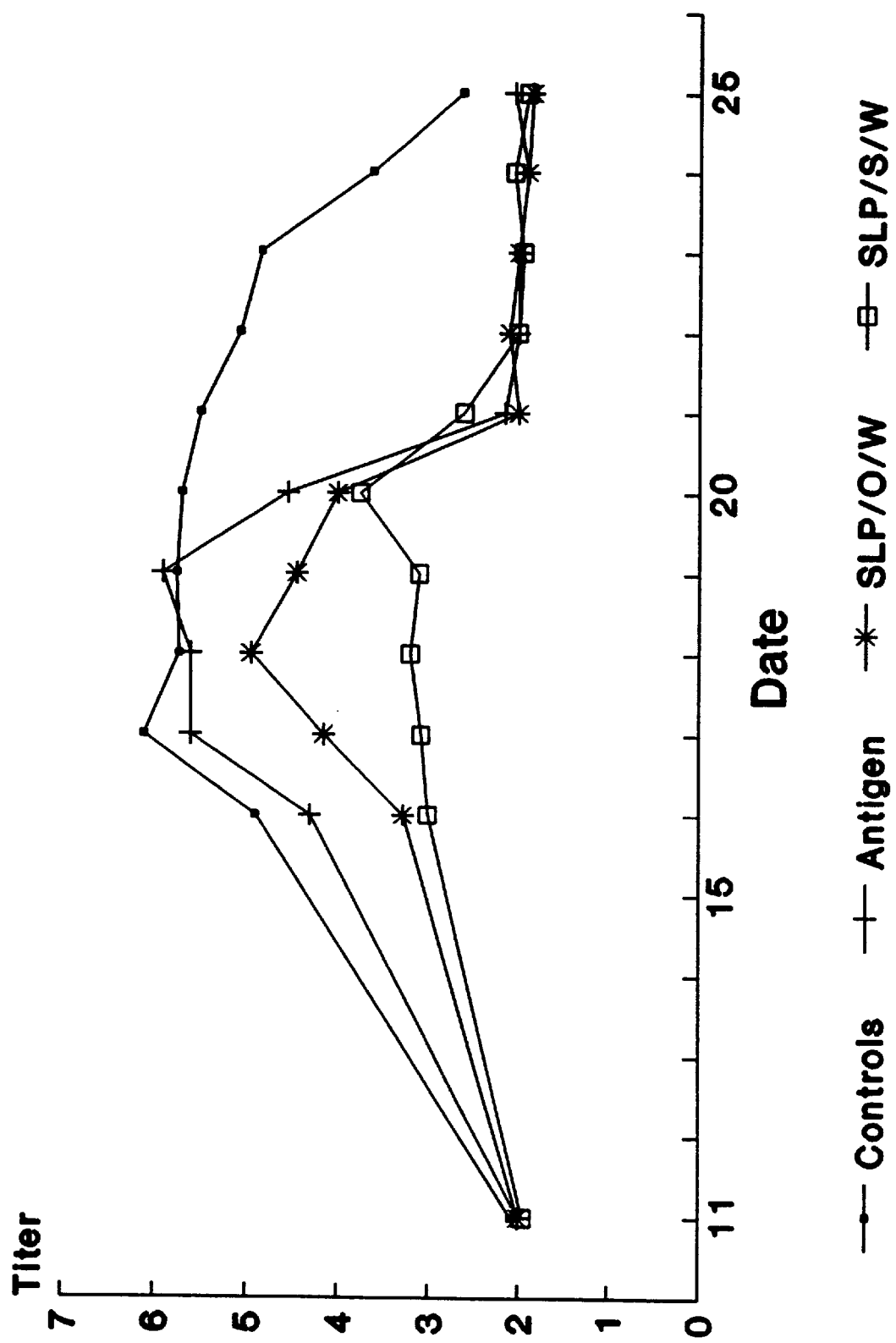
FIG. 1 is a graph depicting the results of the efficacy of live PRV vaccines comprising either SLP/S/W of O/W investigated by measurement of virus excretion after challenge as described in Example 3.

The invention is further illustrated by the following experiments.

EXAMPLE 1

Use of SLP-dispersions as Adjuvants

In the experiments described below, a specific lipophilic sulfolipopolysaccharide (SLP)-derivative was used, (viz. SLP-H2—a SLP-derivative with a mean sulfate:lipid:monosaccharide-ratio of approximately 0.1:0.8:1.0), unless stated otherwise.

Vaccines used in the different experiments were prepared in one of the following manners:

I. SLP was solubilized in the oil phase (squalane) at an appropriate concentration, Solubilization of the SLP could be improved by slightly heating the squalane (70° C.). Subsequently, the oil phase was added to an aqueous phase (phosphate buffered saline, containing 2% TWEEN™ 80) prewarmed at 70° C., and vigorously stirred. The pre-emulsion obtained was emulsified further by either ultrasonic disrupture or microfluidizing. The emulsion was considered to be ready-for-use if the oil droplets were smaller than 1 micrometer (estimated by phase contract microscopy at 1000-fold magnitude). The vaccine was prepared by mixing one volume of adjuvant solution (of about 4° C.) with one volume of antigen solution.

The quantity of SLP indicated is expressed as the sugar content using Ficoli as the reference (dry material is about two fold high).

II. SLP was solubilized in an organic solvent (e.g. ethanol, chloroform or dichloromethane) and mixed with the oil. The solvent was eliminated by extensive evaporation at 60 or 70° C. and low pressure. Subsequently, the oil phase was added to an aqueous phase (phosphate buffered saline, containing 2% TWEEN™ 80) prewarmed at 70° C. under vigorous stirring. The pre-emulsion obtained was emusified further by either ultrasonic disrupture or microfluidizing. The emulsion was considered to be ready-for-use if the oil droplets were smaller than 1 micrometer (estimated by phase contrast microscopy at 1000-fold magnitude). The vaccine was prepared by mixing one volume of adjuvant solution (of about 4° C.) with one volume of antigen solution.

III. SLP was added to the adjuvant solution (e.g. mineral oil-in-water emulsion) and the SLP was dispersed by ultrasonic disrupture. The adjuvant solution was considered to be ready-for-use if no precipate was visible by macroscopy (40-fold magnitude) and microscopy (400- and 1000-fold magnitude). One volume of the adjuvant solution was mixed with one volume of antigen solution.

IV. SLP, oil and aqueous phase with 2% TWEEN™ 80 were put in a vessel, mixed vigorously and subsequently emulsified by ultrasonic disrupture or microfluidizing while maintaining the temperature at about 70° C. The emulsion was considered to be ready-for-use if the oil droplets were smaller than 1 micrometer (estimated by phase contrast microscopy at 1000-fold magnitude). The vaccine was prepared by mixing one volume of adjuvant solution (of about 4° C.) with one volume of antigen solution.

V. SLP was solubilized in an appropriate volume of liquid surface-active agent (e.g. TWEEN™ 80) and the aqueous phase was added under vigorous mixing, resulting in a clear or opalescent suspension. Squalane was added to this suspension and the mixture was emulsified by microfluidizing.

VI. As V except that the SLP in an organic solute was mixed with a liquid surface-active agent (e.g. TWEEN™ 80) and the organic phase was evaporated before or after addition of an aqueous phase.

Although no significant differences were seen in adjuvant activity, preparation methods I, II, V and VI were prefered as these are relatively easy procedures and easily applicable for large scale production.

A typical SLP/S/W (sulfolipopolysaccharide/squalane/water) adjuvanted vaccine comprises per ml the following components: 2.5 mg SLP, 0.05 ml (40 mg) squalane, 0.01 ml (10 mg) TWEEN™ 80. The SLP-derivative used had a mean, lipid/sulfate content (number of groups per monosaccharide units of the polysaccharide) of 0.8/0.1.

EXAMPLE 2

SLP-H2/Squalane/Water as Adjuvant for Various Antigens in Mice and Guinea Pigs Materials and Methods Animals Random Swiss, female mice and guinea pigs were obtained from Harlan, Zeist, The Netherlands. At the age of about 10 weeks, groups of five animals were immunized subcutanously (sc), intraperitoneally (ip), or intramuscularly (im) with 0.2 ml vaccine at Week 0 and 3 and blood was collected at Week 3 and 6, unless stated otherwise.

SLP-H2/Squalane/W Adjuvant

SLP-H2 in an organic solvent (either dichloromethane or chloroform) was mixed with squalane (Sigma Chem. Comp. St. Louis, USA) and the organic solvent was removed by evaporation in a Rotavapor (Büchl Lab.-Technik AG, Switzerland) at low pressure and 60° C. during at least 6 h. The squalane containing the SLP was mixed with phosphate buffered saline containing 2% Tween 80 (PBS/2% TWEEN™ 80) and the mixture was emulsified in two steps. A preemulsion was made by vigorous shaking on a vortex. Subsequently, the preemulsion was microfluidized (Microfluidics Corp. Newton, USA) in two or three cycli with increasing pressure (200 to 600 atmospheres). The emulsion obtained was analyzed by assessment of the size of the oildroplets under the microscope (1000× magnification) and by a microparticle sizer (Malvern Instruments). The emulsification procedure was repeated until most of the droplets had a diameter of less than 1 μm and no particles with a diameter of more than 10 μm were present. Merthiolate was added to the SLP-H2/s/w emulsion at a final concentration of 0.01% and the adjuvant was stored at 4° C. The adjuvant solution used comprised per ml 5 mg SLP, 0.1 ml (80 mg) squalane and 0.02 ml (20 mg) Tween 80, unless stated otherwise.

Vaccine and Vaccinations

The vaccines tested were prepared by mixing one volume of antigen solution with one volume of the adjuvant solution at least one day before injection. Mice received 0.2 ml of one of the following vaccins containing or not an adjuvant:

Vaccine I contained 10 μg dinitrophenylated bovine serum albumin (DNP-BSA) per dose (Experiment I).

Vaccine II contained 10 μg DNP-BSA, 1 μg MRC-11 inactivated influenza virus strain; and 10 μg ovalbumin (OVA) per dose (Experiment II).

Vaccine III contained 1 μg MRC-11 inactivated influenza virus strain; and 10 μg OVA per dose (Experiments III, IV and VI), and Vaccine IV comprised 5log10 TCID50 inactivated pseudorabies virus particles (iPRV), 0.44 μg A/Swine, 0.4 μg MRC-11 inactivated influenza virus strain and 0.2 μg X-79 inactivated influenza virus strain, (Experiment VI). Guinea gigs were injected with vaccine IV with or without adjuvant. The antigenic composition of Vaccine IV is comparable with that of porcine of Suvaxyn iAuj/Flu3 vaccine and one tenth of the dose for pigs if injected into mice or guinea pigs.

The following adjuvants were tested in mice:

1. An emulsion of mineral oil MARKOL™ 52)/phosphate buffered saline plus 1% TWEEN™ 80 (O/W) containing 40 mg of oil per dose (Group 182).
2. An emulsion of SLP/O/W containing per dose 0.5 mg of SLP and 40 mg of mineral oil (MARKOL™ 52; Group 188).
3. An emulsion of squalane/W (S/W) containing 8 mg of squalane per dose (Group 951, 1063, 1083, 1688, and 2322),
4. An emulsion of SLP/S/W containing 0.5 mg of SLP and 8 mg of squalane per dose (Group 952, 953, 1062, 1082, 1691, 1966, and 2334),
5. An emulsion of SLP/S/W containing 1.0 mg of SLP and 8 mg of squalane per doses (Group 1692),
6. An emulsion of SLP/S/W containing 2.5 mg of SLP and 8 mg of squalane per dose (Group 1693),
7. An emulsion of S/W containing 2 mg of squalane per dose (Group 1683),
8. An emulsion of SLP/S/W containing 0.5 mg of SLP and 2 mg of squalane per dose (Group 1685),
9. An emulsion of SLP/S/W containing 1.0 mg of SLP and 2 mg of squalane per dose (Group 1686),
10. An emulsion of SLP/S/W containing 2.5 mg of SLP and 2 mg of squalane per dose (Group 1687),
11. A suspension of SLP in phosphate buffered saline containing TWEEN™ 80 (PBS/T) containing per dose of 0.5 mg of SLP (Group 973, 974, 1061, 1081, 1964, and 2327),
12. A suspension of SLP in phosphate buffered saline containing TWEEN ™ 80 (PBS/T) containing per dose of 0.2 mg of SLP (Group 1962),
13. An emulsion of S/W plus Ficoli containing 8 mg of squalane per dose and 0.5 mg of Ficoli per dose (Group 1998).

The following adjuvants were tested in guinea pigs:

1. An emulsion of O/W containing 40 mg of oil (Markol 52) per dose (Experiment IV, Group 1; Experiment V, group 2),
2. An emulsion of S/W containing 8 mg of squalane per dose (Experiment I; Group 2; Experiment II; Group 4; Experiment III; Group 9; Experiment IV; Group 6; Experiment V; Group 3),
3. An emulsion of SLP/S/W containing 0.5 mg of SLP and 8 mg of squalane per dose (Experiment I; Group 3; Experiment II; Group 5; Experiment III; Group 10; Experiment V; Group 8),
4. An emulsion of SLP/S/W containing 0.25 mg of SLP and 8 mg of squalane per dose (Experiment IV, Group 7).
5. An emulsion of SLP/S/W containing 1.25 mg of SLP and 8 mg of squalane per dose (Experiment IV, Group 8).

The following adjuvants were tested in pigs:

1. An emulsion of O/W containing 400 mg of oil per dose,
2. An emulsion of S/W containing 80 mg of squalane per dose,
3. An emulsion of SLP/S/W containing 5 mg of SLP and 80 mg of squalane per dose, and
4. A suspension of SLP in PBS/T containing 5 mg of SLP per dose.

DETERMINATION OF ANTIBODY TITERS IN SERUM

Anti-DNP-BSA antibody responses were measured by a haemagglutination (HA) reaction using dinitrophenylated sheep red blood cells (DNP-SRBC) as indicator cells. Briefly, serum was serially diluted twofold in saline containing 1% normal rabbit serum (which has been preadsorbed with sheep red blood cells) in round-bottom 96-wells plates and DNP-SRBC suspension was added. The reciprocal serum dilution which just gave agglutination was considered to be the titer.

Anti-OVA antibody responses were measured by heamagglutination of SRBC conjugated with OVA.

Anti-OVA antibody titers were measured by a serum neutralization test (SN). Briefly, serum was serially diluted twofold in 96-wells plates. The serum dilutions were combined with an Aujeszky virus suspension of 100 TCID50. After incubation for 24 h at 37° C., 2.10e4 Pd-5-cells per well were added to the serum-virus mixture. After five days of incubation at 37° C., virus plagues were enumerated and the reciprocal dilution of serum causing 50% neutralized of the virus was considered to be the antibody titer.

Anti-iFlu antibody titers were measured by a haemagglutination inhibition reaction (HI). Sera were pretreated with kaolin by adding one volume of serum to four volumes of kaolin (50 μl plus 200 μl, respectively) in a 96-well round-bottom plate. After incubation for 30 min at room temperature, the kaolin was spun down and the supernatant collected and serially diluted twofoldly in veronal buffered saline containing 0.1% BSA in round-bottom 96-wells plates. Four HA units of influenza virus were added to the wells and plates were incubated for 1 h at room temperature. Chicken red blood cells were washed three times in veronal buffered saline with 0.1% BSA and were added to the wells at a concentration of 0.25%. After 30 minutes and within 2 h, agglutination was detected and the highest reciprocal serum dilution demonstrating inhibition of haemagglutination was considered to be the titer.

Results

Adjuvanticity in Mice

Adjuvanticity of SLP/S/W for the antibody responses against various antigens was studied in mice in six separate experiments (Table 1). The effects of SLP/S/W were compared with either SLP, S/W, O/W, or antigen without adjuvant. Antibody responses against DNP-BSA were enhanced significantly by SLP/S/W but not by O/W (Exp. I). SLP alone was less effective than SLP/S/W and S/W was less effective than both SLP or SLP/S/W (Exp. III). Anti-MRC-11 antibody responses were stimulated significantly by different adjuvants tested. SLP/S/W was more effective than S/W alone (Exp. III to VI) except in Exp. II. SLP alone demonstrated considerable adjuvanticity which was comparable to (Exp. IIIa, IIIb, and VIb) or less than that of SLP/S/W (Exp. II, V, VIa). Anti-MRC-11 antibody response increased with increasing dose of SLP and increasing amount of squalane in SLP/S/W (Exp. V).

Antibody responses against OVA were enhanced by SLP, S/W, and SLP/S/W but SLP/S/W was significantly more effective than SLP or S/W alone (Exp. II, IIIa, IIIb, and IV). Adjuvanticity of SLP/S/W for anti-OVA response did not increase with increasing dose of either SLP or squalane within the range tested.

Humoral response against iPRV were measured and SLP/S/W augmented significantly the response (Exp. VIa and VIb) and proved to be more effective than S/W. SLP alone was about as effective as SLP/S/W.

The results are summarized in Tables 1A and 1B.

TABLE 1A

| Group adjuvant | 2log antibody titers against ||||||
|---|---|---|---|---|---|---|
| | DNP-BSA || MRC-11 || OVA ||
| [mg per dose] | mean | sd | mean | sd | mean | sd |
| Experiment I (ip) | | | | | | |
| 181 — | 4.0 | 0.8 | | | | |
| 182 O/W | 4.8 | 1.8 | | | | |
| 188 SLP/O/W | 9.0 | 2.0 | | | | |
| Experiment II (ip) | | | | | | |
| 951 S/W [8.0] | 2.2 | 1.6 | 7.8 | 1.3 | 5.3 | 2.1 |
| 952 SLP/S/W [8.0] | 8.8 | 1.9 | 3.2 | 1.1 | 8.4 | 1.4 |
| 973 SLP | 8.2 | 0.8 | 3.0 | 1.2 | 5.4 | 2.7 |
| 953 SLP/S/W [8.0] | 9.0 | 1.7 | 4.2 | 1.8 | 4.0 | 1.6 |
| 974 SLP | 7.4 | 0.9 | 1.4 | 0.5 | 4.0 | 1.9 |
| 978 — | 3.4 | 1.5 | 1.4 | 0.9 | 0.8 | 0.8 |
| Experiment IIIa (ip) | | | | | | |
| 1061 SLP | | | 6.2 | 1.8 | 7.4 | 1.3 |
| 1062 SLP/S/W | | | 5.7 | 0.6 | 9.7 | 3.2 |
| 1063 S/W | | | 4.8 | 1.1 | 8.8 | 1.9 |
| 1068 — | | | 3.2 | 1.7 | 6.4 | 1.8 |
| Experiment IIIb (sc) | | | | | | |
| 1081 SLP | | | 3.2 | 1.9 | 5.8 | 0.4 |
| 1082 SLP/S/W | | | 3.6 | 2.2 | 9.0 | 2.5 |
| 1083 S/W | | | 1.6 | 1.5 | 8.8 | 1.3 |
| 1088 — | | | 2.6 | 1.7 | 6.6 | 0.9 |
| Experiment IV (ip) | | | | | | |
| 1683 S/W [2.0] | | | 3.0 | 2.4 | 1.8 | 2.5 |
| 1685 SLP/S/W [0.5/2.0] | | | 4.4 | 2.6 | 2.2 | 1.9 |
| 1686 SLP/S/W [1.0/2.0] | | | 5.4 | 2.1 | 3.8 | 1.9 |
| 1687 SLP/S/W [2.5/2.0] | | | 6.0 | 0.7 | 2.0 | 1.9 |
| 1688 S/W [8.0] | | | 8.6 | 0.5 | 1.8 | 1.9 |
| 1691 SLP/S/W [0.5/8.0] | | | 7.2 | 1.3 | 4.6 | 3.5 |
| 1692 SLP/S/W [1.0/8.0] | | | 9.2 | 1.1 | 2.6 | 2.2 |
| 1693 SLP/S/W [2.5/8.0] | | | 10.6 | 1.1 | 2.2 | 2.3 |
| 1697 — | | | 2.0 | 2.0 | 2.0 | 2.8 |

TABLE 1B

| Group adjuvant | 2log antibody titers against ||||||
|---|---|---|---|---|---|---|
| | MRC-11 || OVA || iPRV ||
| [mg per dose] | mean | sd | mean | sd | mean | sd |
| Experiment V (ip) | | | | | | |
| 1962 SLP [0.2] | 6.4 | 1.8 | 5.6 | 3.0 | | |
| 1964 SLP [0.5] | 7.4 | 1.1 | 3.6 | 1.3 | | |
| 1966 SLP/S/W | 9.0 | 0.7 | 6.6 | 2.3 | | |
| 1998 Flcoll + S/W | 7.2 | 2.4 | 6.2 | 3.6 | | |
| Experiment VIa (ip; three weeks after the first Immunization) | | | | | | |
| 2321 — | 0.2 | 0.4 | | | 1.4 | 1.5 |
| 2322 S/W | 3.8 | 1.5 | | | 1.8 | 1.3 |
| 2327 SLP | 4.2 | 1.5 | | | 4.0 | 2.3 |
| 2334 SLP/S/W | 7.2 | 1.3 | | | 5.2 | 1.5 |
| Experiment VIb (ip; three weeks after the second immunization) | | | | | | |
| 2321 — | 4.8 | 1.8 | | | 6.8 | 1.5 |
| 2322 S/W | 6.6 | 0.8 | | | 7.2 | 1.9 |
| 2327 SLP | 10.4 | 1.1 | | | 10.2 | |
| 2334 SLP/S/W | 10.0 | 1.2 | | | 10.2 | 1.1 |

Adjuvanticity in Guinea Pigs

The effect of SLP/S/W on the antibody response to porcine iPRV+iFlu3 vaccine was compared with that of S/W and O/W in guinea pigs. This animal species has been used extensively as a model for porcine vaccines and antibody responses against both iPRV and iFlu components, and are considered to be indicative for efficacy of the vaccine in pigs.

Groups of five animals were immunized subcutaneously with 0.2 ml of the vaccine at week 0 and at week 3, and antibody titers were measured at week 6. The following vaccine compositions were tested:

a. SLP/S/W for inactivated pseudorabies virus (Table 2; Experiment I–V), b. SLP/S/W for inactivated influenza virus strain A/Swine, MRC-11 and X-79 (Experiment IV and V), and Experiments I–III indicate that antibody titers against iPRV were enhanced significantly by squalane-in-water (S/W) and SLP/S/W, and that SLP/S/W is more effective than S/W.

TABLE 2

| Group Adjuvant | [mg per dose] | 2log antibody titers at week 6 against | | | | | | | |
|---|---|---|---|---|---|---|---|---|---|
| | | iPRV | | A/Swine | | MRC-11 | | X-79 | |
| | | mean | sd | mean | sd | mean | sd | mean | sd |
| Experiment I (iPRV + Flu3) | | | | | | | | | |
| 1 — | | 5.0 | | | | | | | |
| 2 S/W | | 8.4 | | | | | | | |
| 3 SLP/S/W | | 8.2 | | | | | | | |
| Experiment II (iPRV) | | | | | | | | | |
| 3 — | | 7.6 | | | | | | | |
| 4 S/W | | 12.3 | | | | | | | |
| 5 SLP/S/W | | 14.8 | | | | | | | |
| Experiment III (iPRV + iFlu3) | | | | | | | | | |
| 8 — | | 5.0 | | | | | | | |
| 9 S/W | | 6.5 | | | | | | | |
| 10 SLP/S/W | | 9.3 | | | | | | | |
| Experiment IV (iPRV + iFlu3) | | | | | | | | | |
| 1 O/W | | 12.3 | 3.4 | 11.3 | | 13.3 | | 12.1 | |
| 6 S/W | | 10.9 | 1.6 | 8.8 | | 10.3 | | 8.9 | |
| 7 SLP/S/W | [0.25] | 10.5 | 0.8 | 12.3 | | 13.5 | | 12.7 | |
| 8 SLP/S/W | [1.26] | 11.0 | 2.3 | 11.3 | | 12.7 | | 11.9 | |
| Experiment V (iPRV + iFlu3) | | | | | | | | | |
| 1 — | | 9.7 | | 6.9 | 7.9 | 8.6 | | | |
| 2 O/W | | 9.0 | | 10.1 | 9.9 | 8.0 | | | |
| 3 S/W | | 9.4 | | 7.7 | 8.7 | 8.4 | | | |
| 8 SLP/S/W | | 9.8 | | 10.6 | 10.5 | >10.2 | | | |

In experiment IV and V little differences in anti-iPRV antibody titers were seen between the different groups. In these experiments, however, significant differences in anti-iFlu3 antibody titers were seen. SLP/S/W and O/W induced higher antibody titers than S/W or antigen alone. SLP/S/W was as effective as O/W.

EXAMPLE 3

SLP-H2/Squalane/Water as Adjuvant for iPRV, iFlu, and Live PRV in Pigs

Materials and Methods

Pigs

Groups of five pigs at an age of about 10 weeks, were used in the experiments. The animal were immunized intramuscularly with 2.0 ml vaccine at Week 0 and 3 and blood was collected at Week 6.

Vaccines and Vaccinations

The vaccines tested contained on volume of antigen and one volume of adjuvant solution. The antigen solution comprised 6log10 TCID50 inactivated pseudorabies virus particles, 4.4 μg of influenza virus strain A/Swine, 4.0 μg of MRC-11 and 2.0 μg of X-79. The adjuvant solution used was either SLP/S/W (5 mg of SLP per ml adjuvant solution and 80 mg of squalane per ml adjuvant solution) as described earlier or a standard mineral oil-in-water emulsion (50% mineral oil).

Freezedried live PRV was reconstituted in diluent or in adjuvant solution (previously diluted 1:1 with diluent) and injected within 10 min.

Results

Stimulation of Antibody Responses Against iPRV and iFlu3

In five separate experiments, adjuvanticity of SLP/S/W was compared with that of standard O/W in pigs. Groups of at least five pigs were immunized with iPRV+iFLU3 combined with either SLP/S/W or standard O/W or with iPRV+ iFLU3 without adjuvant (Table 3). Anti-iPRV antibody titer measured after immunization with SLP/S/W did not significantly differ from those elicited with O/W ($p>0.20$). In four our of five experiments, three- to four-fold higher titers against the different influenza virus strains were detected after injection with SLP/S/W in comparison to standard O/W. Combination of the results and statistical analysis proved a significant increase in the titers against A/Swine ($p<0.01$), MRC-11 l($p<0.01$) and X79 ($p<0.01$).

TABLE 3

| Group Adjuvant | n | 2log antibody titers against: | | | | | | | |
|---|---|---|---|---|---|---|---|---|---|
| | | iPRV | | A/ Swine | | MRC-11 | | X-79 | |
| | | mean | sd | mean | sd | mean | sd | mean | sd |
| Experiment I | | | | | | | | | |
| 1 SLP/S/W | 5 | 6.8 | 4.8 | 8.8 | 2.3 | 9.8 | 0.6 | 11.0 | 0.7 |
| 2 O/W | 5 | 5.4 | 3.4 | 8.8 | 2.3 | 8.6 | 1.8 | 8.2 | 0.8 |

TABLE 3-continued

| | | 2log antibody titers against: | | | | | | | |
|---|---|---|---|---|---|---|---|---|---|
| | | iPRV | | A/ Swine | | MRC-11 | | X-79 | |
| Group Adjuvant | n | mean | sd | mean | sd | mean | sd | mean | sd |
| Experiment II | | | | | | | | | |
| 1 SLP/S/W | 5 | 9.0 | 0.7 | 7.6 | 2.5 | 13.1 | 1.0 | 9.8 | 0.8 |
| 2 O/W | 5 | 8.0 | 1.2 | 8.2 | 1.6 | 12.6 | 1.6 | 10.4 | 0.8 |
| Experiment III | | | | | | | | | |
| 1 SLP/S/W | 5 | 9.4 | 0.5 | 10.4 | 1.1 | 11.2 | 0.8 | 10.8 | 0.8 |
| 2 O/W | 5 | 10.0 | 0.7 | 9.0 | 3.2 | 11.4 | 1.1 | 10.6 | 1.1 |
| Experiment IV | | | | | | | | | |
| 1 SLP/S/W | 15 | 6.3 | 2.0 | 10.0 | 1.1 | 12.1 | 1.0 | 10.2 | 0.6 |
| 2 O/W | 10 | 6.3 | 0.7 | 7.1 | 1.5 | 8.7 | 1.2 | 7.8 | 1.0 |
| Experiment V | | | | | | | | | |
| 1 SLP/S/W #2L | 5 | 7.8 | 0.5 | 7.2 | 2.7 | 11.4 | 0.5 | 11.0 | 1.4 |
| 2 O/W | 5 | 5.6 | 1.5 | 5.8 | 1.6 | 9.0 | 1.0 | 8.6 | 1.3 |
| Combined results of experiments I to V | | | | | | | | | |
| 1 SLP/SAW | 35 | 7.4 | 2.0 | 9.1 | 1.6 | 11.6 | 1.1 | 10.6 | 0.8 |
| 2 O/W | 30 | 69 | 1.5 | 7.3 | 1.8 | 9.8 | 1.2 | 9.1 | 0.9 |
| Factor of increase | | 1.4 | | 3.5 | | 3.5 | | 2.8 | |
| P value | | >0.20 | | <0.01 | | <0.01 | | <0.01 | |
| Significance | | NS | | S | | S | | S | |

Groups of n pigs were immunized im with iPRV+iFlu3 plus adjuvant at Week 0 and 3.

Antibody titers were measured at Week 6. Factor of increase was calculated by the following formula: 2e(titer with SLP/S/W−titer with O/W). P values of the differences between SLP/S/W and O/W were calculated by the student's test. Values of >0.05 were considered to be not significant. NS: not significant; S: significant. Four out of the 15 animals of group 1 of experiment IV did not develop a significant antibody response against influenza strain MRC-11 (mean titer in these animals was <5.6) but normal responses against the other antigens were measured.

TABLE 4

| | | 2 log antibody titers against PRV at: | | | |
|---|---|---|---|---|---|
| | | Week 3 | | Week 6 | |
| Group adjuvant | n | mean | sd | mean | sd |
| Experiment I | | | | | |
| 1 — | 5 | .6 | 0.9 | 7.4 | 1.7 |
| 2 O/W | 5 | 5.2 | 1.1 | 10.2 | 1.3 |
| 3 SLP/S/W | 5 | 6.2 | 0.8 | 12.0 | 0.0 |
| Experiment II | | | | | |
| 1 O/W | 5 | 6.8 | 1.5 | 11.8 | 2.6 |
| 2 SLP/S/W | 5 | 5.5 | 1.8 | 13.6 | 3.0 |
| 5 — | 5 | 3.5 | 1.0 | 9.0 | 0.9 |
| Experiment III | | | | | |
| 1 — | 5 | 2.4 | 0.5 | 7.4 | 1.1 |
| 2 SLP | 5 | 3.8 | 0.4 | 9.0 | 1.6 |
| 4 O/W | 5 | 4.8 | 1.3 | 10.2 | 1.1 |
| 5 SLP/S/W | 5 | 4.6 | 0.9 | 11.6 | 0.5 |
| Experiment IV | | | | | |
| 1 — | 5 | | | 6.0 | 1.0 |

TABLE 4-continued

| 2 SLP/S/W | 5 | | | 11.0 | 0.7 |
|---|---|---|---|---|---|
| 3 O/W | 5 | | | 8.8 | 0.4 |
| Combined results of Experiments I and IV | | | | | |
| 1 — | 20 | | | 7.5 | 1.1 |
| 2 O/W | 20 | | | 10.3 | 1.4 |
| 3 SLP/S/W | 20 | | | 12.0 | 1.4 |

| | Factor of increase | P value | significant |
|---|---|---|---|
| O/W versus '—' | 7.0 | <0.01 | significant |
| SLP/S/W versus O/W | 3.4 | <0.01 | significant |
| SLP/S/W versus '—' | 23.0 | <0.01 | significant |

Stimulation of Antibody Responses Against Live PRV

In four separate experiments, the effects of SLP/S/W and standard O/W on the antibody responses against live PRV were studied. Pigs were vaccinated twice and anti-PRV antibody titers were measured three weeks after each vaccination. In all cases, low to moderate antibody titers were observed after the first injection and titers increased by the second immunization (Table 4). In comparison to live PRV in diluent, SLP/S/W and O/W enhanced slightly the antibody titers after the first immunization. After the second vaccination antibody titers were increased significantly by SLP/S/W and O/W.
SLP/S/W induced a 23-fold increase while O/W evoked an seven-fold increase in anti-PRV antibody titers.

Reduction of Virus Excretion After Challenge by Imunization with Live PRV Plus SLP/S/W as Adjuvant Efficacy of live PRV vaccines comprising either SLP/S/W or O/W was investigated by measurement of virus excretion after challenge. Animals were challenged intranasaly five weeks after the second immunization and virus titers in tonsillar swabs were monitored during 14 subsequent days (FIG. 1). Titers are expressed as 10log $TCID_{50}$.

Nonvaccinated animals excreted large quantaties of PRV from 11 to 24 days after challenge. Two out of five animals of this control group died within the period of examination. Immunization of the animals without adjuvant reduced both the period and the titer of virus excreted.

Vaccination with PRV reconstituted in either SLP/S/W or O/W caused further reduction of the period of excretion and the amount of virus excreted. With O/W, virus titers at least 4log10 were excreted during four days while with SLP/S/W a maximal virus titer of 3.5log10 was measured at only a single day. Total virus excretion was determined by calculation of the area under the curve (AUC) of the log virus titer versus the time interval after challenge. The AUC of control animals was considered to be 100%. AUC of animals which received antigen without adjuvant was 57%. Vaccination with O/W and SLP/S/W resulted in AUCs of 39% and 26%, respectively.

EXAMPLE 4

Adjuvanticity in Chicken

Groups of ten chickens were immunized with 0.5 ml vaccine at Week 0 and 3 and antibody titers were measured at Week 0, 3 and 6, SLP/S/W mixed with inactivated Newcastle disease (NCD) virus. The results are summarized in Table 5.

TABLE 5

| group | adjuvant | mean 2 log antibody titers against NCD at Week: | | |
|---|---|---|---|---|
| | | 0 | 3 | 6 |
| 1 | W/O | 4.0 | 10.0 | 10.0 |
| 2 | — | 4.0 | 5.6 | 8.1 |
| 3 | SLP/S/W | 4.0 | 7.3 | 8.5 |

EXAMPLE 5

Immunomodulatory Activity Versus Immunoadjuvanticity

Effects of a hydrophilic SLP-derivative with proven stimulatory activity on non-specific resistance (Patent publication EP 295,749) on specific immune responses were studied. In different animal models, the adjuvanticity of the hydrophobic SLP-derivative with a mean sulfate/lipid-ratio of 0.1/0.8 was compared with that of a hydrophilic SLP-derivative with a mean sulfate/lipid-ratio of 0.6/0.01 or 1.6/0.8. The different SLP/S/W emulsions were prepared by adding the SLP to an emulsion of S/W with oil droplets of less than 1 micrometer and subsequent ultrasonication of the emulsion. Groups of five mice or guinea pigs were immunized so with 0.2 ml of a vaccine comprising per dose 0.5 mg of SLP-derivative and 8 of mg squalane. Pigs were immunized with 2.0 ml of vaccine comprising per dose 5 mg of SLP-derivative and 80 mg of squalane.

Results are shown in Table 6.

TABLE 6

| Group | sulfate/IIp Id ratio | mean (± SEM) 2 log antibody titers at week 6 | against |
|---|---|---|---|
| Experiment I (mice) | | | |
| 1 | 0.1/0.8 | 9.7 + 3.2 | ovalbumin |
| 2 | 0.6/0.01 | 6.0 + 1.0 | ovalbumin |
| Experiment Ib (mice) | | | |
| 1 | 0.1/0.8 | 9.0 + 2.5 | ovalbumin |
| 2 | 0.6/0.01 | 4.8 + 0.8 | ovalbumin |
| Experiment II (guinea pigs) | | | |
| 1 | 0.1/0.8 | 13.1 ± 2.5 | PRV |
| 2 | 1.6/0.8 | 7.7 ± 2.3 | PRV |
| Experiment IIIa (pigs) | | | |
| 1 | 0.1/0.8 | 4.3 ± 1.2 | PRV |
| 2 | 0.6/0.01 | <0.5 ± 0.0 | PRV |
| Experiment IIIb | | | |

TABLE 6-continued

| Group | sulfate/IIp Id ratio | mean (± SEM) 2 log antibody titers at week 6 | against |
|---|---|---|---|
| 1 | 0.1/0.8 | 8.5 ± 1.0 | A/Swine |
| 2 | 0.6/0.01 | <2.7 ± 0.9 | A/Swine |
| Experiment IIIc | | | |
| 1 | 0.1/0.8 | >10.5 ± 0.5 | X-79 |
| 2 | 0.6/0.01 | 6.5 ± 0.8 | X-79 |
| Experiment IIId (pigs) | | | |
| 1 | 0.1/0.8 | >9.8 ± 1.0 | MRC-11 |
| 2 | 0.6/0.01 | 6.3 ± 1.4 | MRC-11 |

From the results of the experiments with different antigens and in different animal species it can be clearly observed that the hydrophobic SLP in S/W is a more effective adjuvant than the hydrophilic SLP in S/W.

We claim:

1. Adjuvant composition comprising at least one synthetic hydrophobic lipopolysaccharide, an interface-forming constituent and optionally an aqueous solute; wherein said lipopolysaccharide has a hydrophilic-lipophilic-balance (HLB) value with the range of 4 (inclusive) to 9 (exclusive).

2. Adjuvant composition according to claim 1 wherein said lipopolysaccharide has a mean ratio of lipid groups to sugar groups of between 0.2 to 4.

3. Adjuvant composition according to claim 1 or 2 wherein said lipopolysaccharide is provided with anionic groups with maintaining the overall hydrophobicity.

4. Adjuvant composition according to claim 1 or 2 wherein said interface-forming constituent is a liquid immiscible with an aqueous phase.

5. Adjuvant composition according to claim 1 or 2 wherein said interface-forming constituent is a solid insoluble in an aqueous phase.

6. Vaccine comprising an adjuvant according to claim 1 or 2 and an immunogen.

7. Vaccine comprising an adjuvant composition comprising at least one synthetic hydrophobic lipopolysaccharide, an interface-forming constituent and optionally an aqueous solute according to claim 1 wherein said lipopolysaccharide is provided with anionic groups while maintaining the overall hydrophobicity, and an immunogen.

8. A vaccine according to claim 7 wherein said interface-forming constituent is selected from the group consisting of a liquid immiscible with an aqueous phase and a solid insoluble in an aqueous phase.

* * * * *